(12) United States Patent
Miyamoto

(10) Patent No.: US 8,933,926 B2
(45) Date of Patent: Jan. 13, 2015

(54) IMAGE PROCESSING APPARATUS, METHOD, AND PROGRAM

(75) Inventor: Masaki Miyamoto, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 782 days.

(21) Appl. No.: 12/736,382

(22) PCT Filed: Mar. 31, 2009

(86) PCT No.: PCT/JP2009/001494
§ 371 (c)(1),
(2), (4) Date: Dec. 2, 2010

(87) PCT Pub. No.: WO2009/122724
PCT Pub. Date: Oct. 8, 2009

(65) Prior Publication Data
US 2011/0115785 A1 May 19, 2011

(30) Foreign Application Priority Data
Apr. 3, 2008 (JP) .................................. 2008-097205

(51) Int. Cl.
*G06T 15/00* (2011.01)
*G06T 17/00* (2006.01)
*G06T 15/50* (2011.01)
*A61B 6/00* (2006.01)
*A61B 8/08* (2006.01)
*G06T 15/08* (2011.01)

(52) U.S. Cl.
CPC ............... *G06T 15/503* (2013.01); *A61B 6/466* (2013.01); *A61B 8/483* (2013.01); *G06T 15/08* (2013.01)
USPC .......................................... 345/419; 345/424

(58) Field of Classification Search
CPC .................... G06T 15/08; G06T 2207/30004; G06T 2210/41; G06T 2207/20144; G06T 7/0012; G06T 7/0042
USPC .......................................................... 345/419
See application file for complete search history.

(56) References Cited

U.S. PATENT DOCUMENTS 5,566,282 A * 10/1996 Zuiderveld .................... 345/424
6,058,218 A    5/2000 Cline (Continued)

FOREIGN PATENT DOCUMENTS

| JP | 11-242739 | 9/1999 |
| JP | 2006-000127 | 1/2006 |
| JP | 2006-055213 | 3/2006 |

*Primary Examiner* — Kee M Tung
*Assistant Examiner* — Haixia Du
(74) *Attorney, Agent, or Firm* — Jean C. Edwards, Esq.; Edwards Neils PLLC

(57) ABSTRACT

When generating a projection image by setting a plurality of search points in an intended display area of a three-dimensional image along a plurality of visual lines, each connecting each pixel on a projection plane on which the three-dimensional image is projected and an arbitrary viewpoint, calculating a pixel value of each search point by an interpolation operation based on pixel values of adjacent pixels of each search point, and determining a pixel value of each pixel on the projection plane with respect to each visual line based on the calculated pixel value of each search point, if an adjacent pixel of a search point is a pixel in an unintended display area, the pixel value of the search point is calculated such that the pixel value of the pixel in the unintended display area does not contribute to the calculation, thereby preventing an artifact arising from the unintended display area.

13 Claims, 3 Drawing Sheets

(56) References Cited

U.S. PATENT DOCUMENTS

| | | | |
|---|---|---|---|
| 7,474,308 B2 * | 1/2009 | Deering | 345/419 |
| 2006/0056726 A1 | 3/2006 | Fujiwara et al. | |
| 2006/0202989 A1 * | 9/2006 | Yinghui | 345/424 |
| 2008/0231632 A1 * | 9/2008 | Sulatycke | 345/424 |

* cited by examiner

IMAGE PROCESSING APPARATUS, METHOD, AND PROGRAM

BACKGROUND OF THE INVENTION

1. Field of the Invention

The present invention relates to three-dimensional image processing and, more particularly, to processing for generating a projection image from a three-dimensional image which includes an unintended display area.

2. Description of the Related Art

In the medical field, observation and diagnosis of projection images which are three-dimensional medical images, obtainable by CT systems, MRI systems, ultrasonic diagnostic systems, or the like, projected on desired projection planes are performed. In order to obtain such a projection image, image processing, in which a plurality of search points is determined in a three-dimensional medical image along a visual line passing from an arbitrary viewpoint to each projected pixel and, based on pixel values of the plurality of determined search points, pixel values of projected pixels are obtained with respect to each visual line, is performed. Such type of known image processing includes, for example, MIP (Maximum Intensity Projection) processing in which a maximum pixel value of search points is extracted with respect to each visual line and projected, MinIP (Minimum Intensity Projection) processing in which a minimum pixel value of search points is extracted with respect to each visual line and projected, and the like.

It is also known that, prior to generating a projection image, an unintended display area is determined in a three-dimensional medical image and image processing is performed on an intended display area. For example, a method that generates, from a three-dimensional cardiac image that includes a blood pool of aorta, which is not a display target, and coronary artery, which is a display target, an enhanced image that includes the coronary artery but not the blood pool through predetermined image processing and performs MIP processing on the enhanced image, thereby generating and displaying an image in which the coronary artery is enhanced without being influenced by the blood pool of unintended display target is proposed as described, for example, in Japanese Unexamined Patent Publication No. 11(1999)-242739.

When generating a projection image, the position of each search point on a visual line may possibly have a non-integer coordinate value in a coordinate system of three-dimensional image, depending on the positional relationship between the viewpoint and projection plane, so that there may be a case in which the pixel value of each pixel of a three-dimensional image can not be used directly. In such a case, it is necessary to calculate the pixel value of each search point by an interpolation operation based on the pixel values of pixels adjacent to each search point.

Now, when a three-dimensional image is divided into an intended display area and an unintended display area, a search point near the boundary of the two areas naturally lies in the intended display area but a pixel adjacent to the search point may possibly lie in the unintended display area. FIG. 4 shows such an example case, in which one pixel Q $(x_1, y_2, z_2)$ of eight pixels adjacent to a search point $P_{ji}$ (x, y, z) on a visual line $E_j$ is a pixel in an unintended display area.

In such a case, if the pixel value of the search point $P_{ji}$ is calculated by an interpolation operation of adjacent pixel values, the result is influenced by the pixel value of adjacent pixel Q which is supposed to be an unintended display target. For example, when a pixel having a pixel value exceeding a pixel value threshold of 100 is assumed to be an unintended display target (non-display), the pixel value of adjacent pixel Q is 200, the pixel value of each of the other adjacent pixels (in the intended display area) is 100, and the search point $P_{ji}$ lies in the center of each of the adjacent pixels, the pixel value of the search point $P_{ji}$ obtained by the interpolation operation is, $100 \times (\frac{1}{8}) \times 7 + 200 \times (\frac{1}{8}) = 112.5$, which is greater than the threshold value representing the maximum value of display target pixel value, i.e., the value which should be determined as an unintended display pixel value. Here, if a projection image is generated by MIP processing, the pixel value of the search point is used on the visual line having this search point, whereby it appears as an artifact in the projection image.

The present invention has been developed in view of the circumstances described above, and it is an object of the present invention to provide an apparatus and method capable of preventing an artifact arising from an unintended display area when generating a projection image produced by projected pixels of a three-dimensional image that includes an unintended display area. It is a further object of the invention to provide a computer readable recording medium on which is recorded a program for causing a computer to perform the method.

SUMMARY OF THE INVENTION

An image processing apparatus of the present invention is an apparatus including a projection image generation means for setting a plurality of search points in a three-dimensional image along a plurality of visual lines, each connecting each pixel on a projection plane on which the three-dimensional image is projected and an arbitrary viewpoint, calculating a pixel value of each search point by an interpolation operation based on pixel values of adjacent pixels of each search point, determining a pixel value of each pixel on the projection plane with respect to each visual line based on the pixel values of the search points, and generating a projection image formed of each pixel on the projection plane, wherein:

the three-dimensional image is an image divided into an intended setting area in which the search points are intended to be set and an unintended setting area in which the search points are not intended to be set; and if an adjacent pixel of a search point is a pixel in the unintended setting area, the projection image generation means is a means for calculating the pixel value of the search point such that the pixel value of the adjacent pixel in the unintended setting area does not contribute to the calculation.

An image processing method of the present invention is a method including the steps of setting a plurality of search points in a three-dimensional image along a plurality of visual lines, each connecting each pixel on a projection plane on which the three-dimensional image is projected and an arbitrary viewpoint, calculating a pixel value of each search point by an interpolation operation based on pixel values of adjacent pixels of each search point, determining a pixel value of each pixel on the projection plane with respect to each visual line based on the pixel values of the search points, and generating a projection image formed of each pixel on the projection plane, wherein:

the three-dimensional image is an image divided into an intended setting area in which the search points are intended to be set and an unintended setting area in which the search points are not intended to be set; and when calculating a pixel value of each search point, if an adjacent pixel of a search point is a pixel in the unintended setting area, the pixel value of the search point is calculated such that the pixel value of the adjacent pixel in the unintended setting area does not contribute to the calculation.

Further, an image processing program of the present invention is a program for causing a computer to perform the method described above.

The image processing apparatus, method, and program will now be described in detail.

Although the "three-dimensional image" is an image divided into an intended setting area in which the search points are intended to be set and an unintended setting area in which the search points are not intended to be set, it is not necessary that the both areas are set but only either one of them needs to be set explicitly.

The "intended setting area" is a possible area to be displayed when displaying a projection image generated from the three-dimensional image in the present invention.

Specific methods for dividing into "intended setting area" and "unintended setting area" may include, for example, a method that divides into the two areas based on a magnitude relation with respect to a predetermined threshold, a method that sets an area extracted by known image recognition processing to either one of the areas, and the like.

The "arbitrary viewpoint" may be single or plural. That is, the projection image may be an image generated by central projection method in which pixels of a three-dimensional image are projected along a plurality of visual lines from a single viewpoint or an image generated by parallel projection method in which pixels of a three-dimensional image are projected along parallel visual lines from a plurality of viewpoints.

The range of "adjacent pixels" may be set appropriately according to the interpolation method. For example, in the case of linear interpolation, 2×2×2=8 pixels surrounding the search point are regarded as the adjacent pixels, and in the case of tricubic interpolation, 4×4×4=64 pixels surrounding the search point are regarded as the adjacent pixels.

Specific processing examples for "determining a pixel value of each pixel on the projection plane with respect to each visual line based on the pixel values of the search points" may include NIP (Maximum Intensity Projection) processing in which a maximum value of pixel values of all search points on each visual line is determined as the pixel value of each pixel, MinIp (Minimum Intensity Projection) processing in which a minimum value of pixel values of all search points on each visual line is determined as the pixel value of each pixel, a method in which an average value of pixel values of all search points on each visual line is obtained, volume rendering using ray casting, and the like. The advantageous effects of the present invention will become more significant when processing that determines the pixel value of a specific search point on a visual line as the pixel value of a pixel on the projection plane, such as the MIP processing and MinIP processing among those described above.

As for the specific method for realizing "if an adjacent pixel of a search point is a pixel in the unintended setting area, the pixel value of the search point is calculated such that the pixel value of the adjacent pixel in the unintended setting area does not contribute to the calculation", a method in which the pixel value of the pixel in the unintended setting area is replaced with another value and the post replacement value is used in the interpolation operation as the pixel value of the pixel in the unintended area, or a method in which the presence of the adjacent pixel itself in the unintended setting area, as well as the pixel value thereof, is excluded from the interpolation operation, and the interpolation operation is performed using only the other adjacent pixels in the intended target area is conceivable.

In the former case, another value for the replacement can be a value calculated from a pixel value of a pixel in the intended setting area using a method predetermined according to a determination method of the pixel values of the pixels on the projection plane or a fixed value determined according to a determination method of the pixel values of the pixels on the projection plane.

Here, specific examples of the "value calculated by the predetermined method" for the replacement may include maximum value, minimum value, average value, median value, and mode value of pixel values of pixels in the intended setting area, class value of the highest frequency class in a pixel value histogram of each pixel in the intended setting area, maximum value, minimum value, average value, and median value of pixel values of adjacent pixels in the intended setting area adjacent to the search point with respect to the adjacent pixel in the unintended setting area, and the like. As for the specific example of the "predetermined fixed value" for the replacement, maximum or minimum value in the specification of quantization of the three-dimensional image or the like may be used.

Further, as for the specific combination of the determination method of the pixel values of the pixels on the projection plane and the method of calculating a value for the replacement from a pixel value of a pixel in the intended setting area predetermined according the determination method, a combination of a determination method in which the pixel value of a pixel on the projection plane is determined as a maximum/minimum value of pixel values of all search points on a visual line corresponding to the pixel (MIP/MinIP processing) and a predetermined method in which a value not greater than a maximum value or a value not less than a minimum value of pixel values of pixels in the intended setting area is determined as the post replacement value, or a combination of a determination method in which the pixel value of a pixel on the projection plane is determined as a maximum/minimum value of pixel values of all search points on a visual line corresponding to the pixel (MIP/MinIP processing) and a predetermined method in which a value not greater than a maximum value or a value not less than a minimum value of pixel values of adjacent pixels in the intended setting area is used as the post replacement value may be cited. Further, in these cases, the advantageous effects of the invention will become more significant if the three-dimensional image is divided such that the pixel value of a pixel in the unintended setting area is greater/smaller than the pixel value of a pixel in the intended setting area.

According to the present invention, when generating a projection image formed of each pixel on a projection plane by setting a plurality of search points in a three-dimensional image along a plurality of visual lines, each connecting each pixel on the projection plane on which the three-dimensional image is projected and an arbitrary viewpoint, calculating a pixel value of each search point by an interpolation operation based on pixel values of adjacent pixels of each search point, and determining a pixel value of each pixel on the projection plane with respect to each visual line based on the calculated pixel value of each search point, if an adjacent pixel of a search point is a pixel in an unintended search point setting area, the pixel value of the search point is calculated such that the pixel value of the pixel in the unintended search point setting area does not contribute to the calculation. Thus, a pixel value of a pixel in an unintended setting area does not influence in determining a pixel value of each pixel on a projection plane, whereby an artifact arising from an unintended setting area may be prevented.

Further, when determining the pixel value of each pixel on the projection plane, if a processing that determines a pixel value of a specific search point on a visual line as the pixel value of the pixel on the projection plane corresponding to the visual line and if an adjacent pixel in an unintended setting area is included in adjacent pixels of the specific search point, the pixel value of the pixel corresponding to the visual line passing through the specific search point is influenced largely by the adjacent pixel in the unintended setting area, so that the artifact prevention effect of the present invention will become more significant.

DESCRIPTION OF THE PREFERRED EMBODIMENTS

Hereinafter, an embodiment of the present invention will be described with reference to the accompanying drawings.

Figure 1:
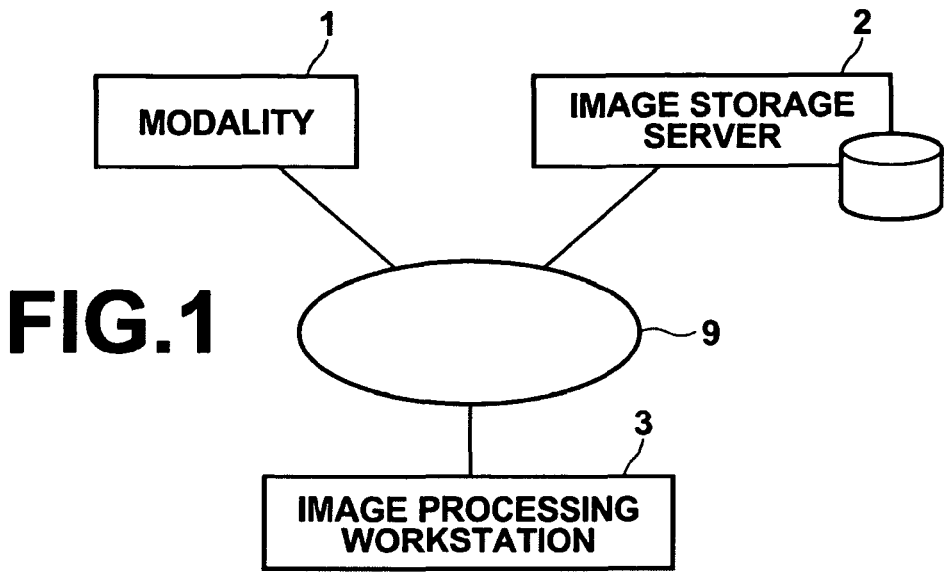
FIG. 1 is a schematic configuration diagram of a three-dimensional medical image processing system according to an embodiment of the present invention.

FIG. 1 is a hardware configuration diagram of a three-dimensional medical image processing system according to an embodiment of the present invention, illustrating an overview thereof. As shown in FIG. 1, the system includes modality 1, image storage server 2, and image processing workstation 3 communicatably linked to each other via network 9.

Modality 1 is a system for obtaining a three-dimension medical image V representing a test body and more specifically, it is a CT system, an MRI system, an ultrasonic diagnostic system, or the like.

Image storage server 2 is a computer for storing in a database and managing the three-dimensional medical image V obtained by modality 1 and a medical image generated through image processing performed in image processing workstation 3, and includes large capacity external memory unit and database management software (e.g., object relational database (ORDB) management software).

Image processing workstation 3 is a computer for performing, in response to a request from a radiologist, image processing on a three-dimensional medical image V obtained from modality 1 or image storage server 2 and displaying a generated image. It includes, in particular, an input device, such as a keyboard, a mouse, or the like, for receiving a request from a radiologist, a main storage unit with a capacity sufficient of storing an obtained three-dimensional medical image V, and a display for displaying a generated image.

The storage format of image data and conmmunication between each component of the system via network 9 are based on a protocol, such as DICOM (Digital Imaging and Communication in Medicine) or the like.

Figure 2:
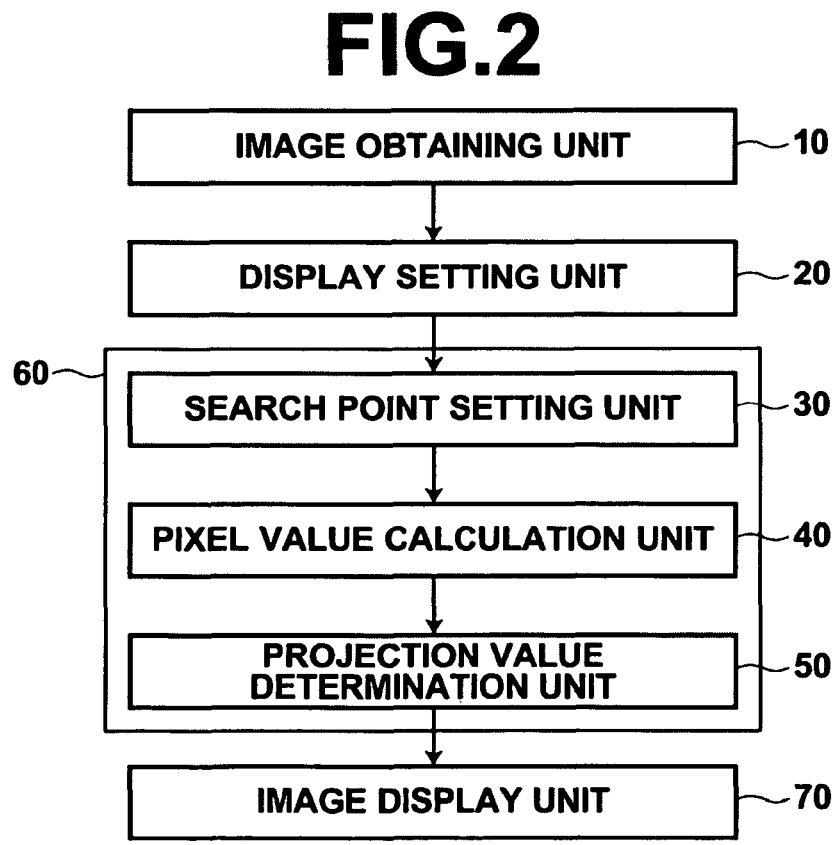
FIG. 2 is a block diagram, illustrating a projection image generation function of the image processing workstation shown in FIG. 1 and a process flow thereof.

FIG. 2 is a block diagram, illustrating a portion of image processing workstation 3 related to the projection image generation function. As shown in the drawing, image processing workstation 3 includes image obtaining unit 10 for obtaining a three-dimensional medical image V of a target patient for radiology reading from modality 1 or image storage server 2 in response to a request from a radiologist, display setting unit 20 for setting an intended display area and a non-display area, projection image generation unit 60 for setting a plurality of search points in the intended display area of the three-dimensional medical image V along a plurality of visual lines, each connecting an arbitrary point and each pixel on a projection plane, determining, based on pixel values of all search points on each visual line, the pixel value of pixel projected on the projection plane by each visual line, and generating a projection image, and image display unit 70 for displaying the generated volume rendering image on a display. Projection image generation unit 60 includes search point setting unit 30, pixel value calculation unit 40, and projection value determination unit 50.

Next, processing performed in each unit described above and a process flow of the medical image processing system, in particular, of image processing workstation 3 for generating a projection image will be described.

First, image obtaining unit 10 obtains a three-dimensional medical image V of a target patient for radiology reading from modality 1 or image storage server in response to a request from a radiologist. The three-dimensional medical image V is generated by dividing a multi-slice image into pixels (voxels) and arranging the pixels in a three-dimensional coordinate space, in which the position of each pixel is defined by a three-dimensional coordinate system with left-right directions of a subject as x-axis, front-back directions as y-axis, and up-down directions as z-axis, and the pixel value of each pixel is related to the coordinates of the position of the pixel.

Next, display setting unit 20 sets an intended display area (intended search point setting area) and a non-display target area (unintended search point setting area) in the three-dimensional image V obtained by image obtaining unit 10. For example, display setting unit 20 generates, based on input from a radiologist specifying such that a partial area of a three-dimensional medical image V is displayed or not displayed, a mask having display/non-display information with respect to each pixel of the three-dimensional medical image V.

Further, the pixel value of a pixel in a non-display area may be set greater/smaller than the pixel value of a pixel in an intended display area by threshold processing, a living tissue area extracted from a three-dimensional medical image V by recognizing the boundary between different living tissues based on a variation in the pixel value or opacity (edge information) may be set so as to be displayed distinguishably from other areas or not displayed, and a mask having display/non-display information with respect to each pixel of the three-dimensional medical image V may be generated by the setting.

Still further, an intended display area and a non-display area may be set in a three-dimensional medical image V by a method different from those described above by way of example, such as a method in which a plurality of sample images, each including a desired target area to be extracted, is machine learned in advance, then the target area is extracted from a three-dimensional medical image V based on the learned result, and the extracted area is displayed distinguishably from other areas or not displayed.

Then, projection image generation unit 60 obtains pixel values of pixels for forming a projection image (output pixel values) through search point setting unit 30, pixel value calculation unit 40, and projection value determination unit 50 with the three-dimensional medical image V having the intended display area and non-display area set by display setting unit 20 as input.

Figure 3:
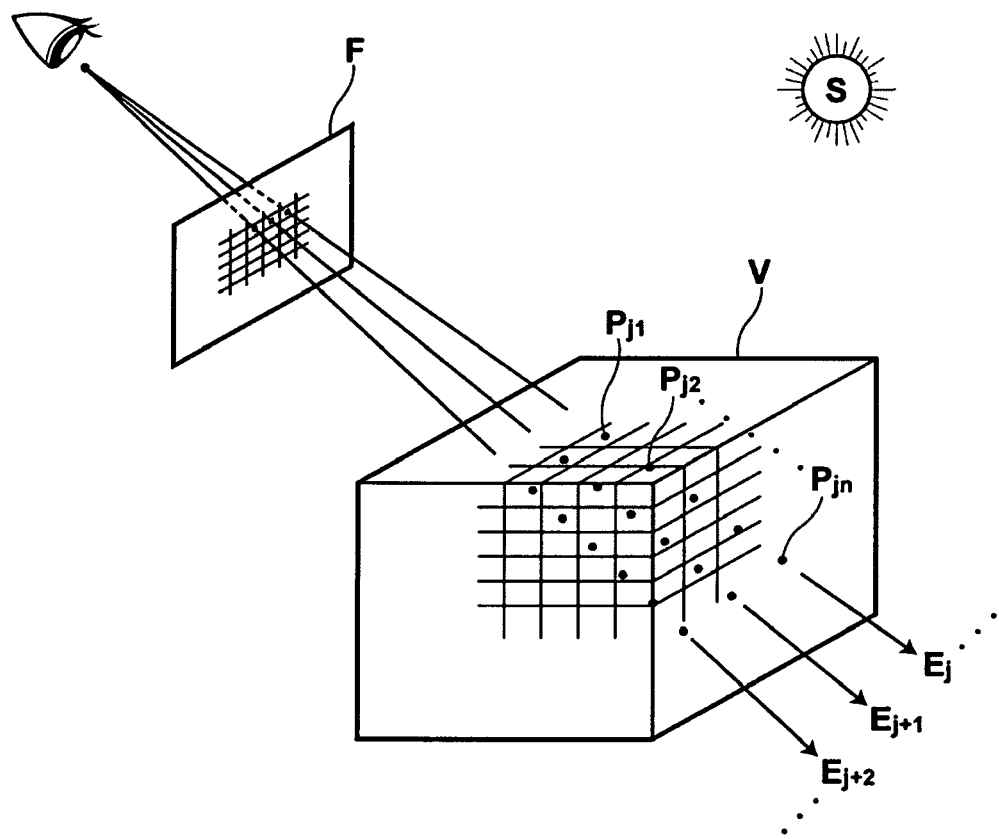
FIG. 3 is a drawing for explaining search point setting by the projection image generation unit.

First, search point setting unit 30 sets, based on a viewpoint E and a projection plane F (size, position, and number of pixels) set from an initial setting file or by input from a radiologist through a mouse or a keyboard, for example, a plurality of search points $P_{ji}$(i=1, 2, - - - , n; n represents the number of search points on a visual line $E_j$) by sampling the intended display area of the three-dimensional medical image V at a predetermined interval along a plurality of visual lines $E_j$ connecting the viewpoint E and each pixel on the projection plane F, as shown in FIG. 3.

Next, pixel value calculation unit 40 determines whether or not each of eight pixels adjacent to each search point $P_{ji}$ (adjacent pixels) is a pixel set as non-display (pixel in the non-display area) with reference to the mask having display/non-display information for each pixel provided by display setting unit 20, if determined to be a pixel set as non-display, replaces the pixel value of the adjacent pixel through replacement processing, to be described later, and then calculates a pixel value g ($P_{ji}$) at each search point $P_{ji}$ by an interpolation operation based on pixel values of adjacent pixels of each search point.

The replacement process described above is a process for calculating the pixel value of a search point $P_{ji}$ such that the pixel value of an adjacent pixel in a non-display area does not contribute to the pixel value of a search point P. Where a projection value is determined by MIP/MinIP processing in projection value determination unit 50, to be described later, the pixel value of an adjacent pixel in the non-display area may be replaced with a maximum/minimum value of pixel values of all pixels in the intended display area or with a maximum/minimum value of pixel values of other adjacent pixels of the search point in the intended display area.

Figure 4:
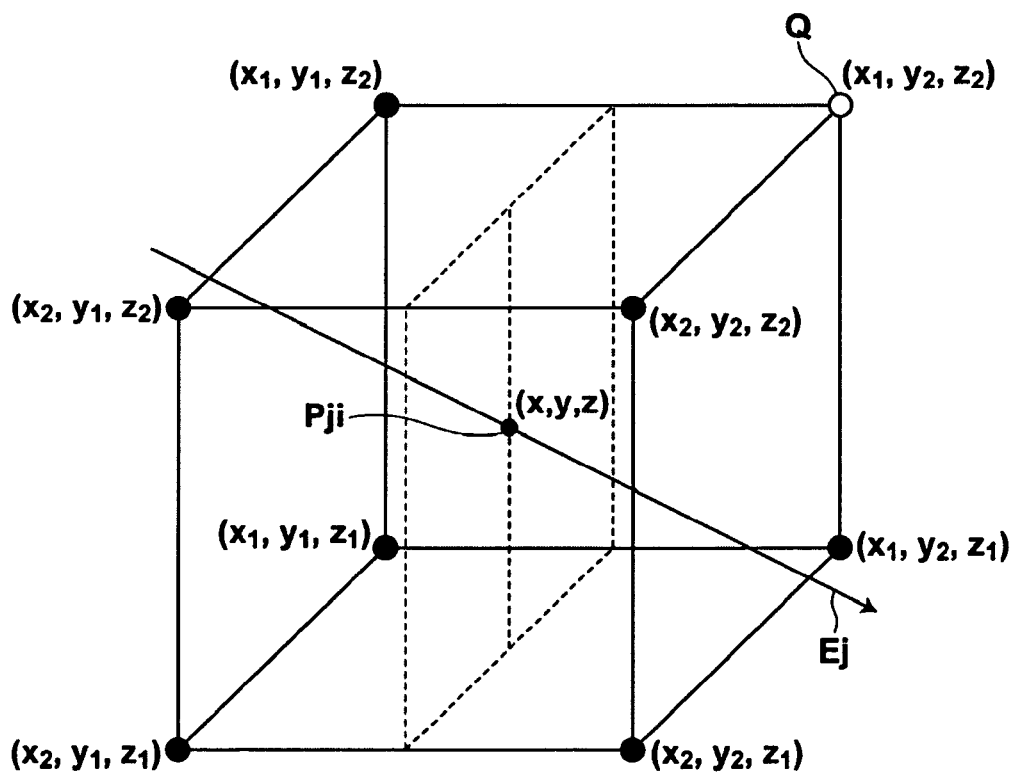
FIG. 4 is a drawing for explaining the calculation of pixel value of a search point by the pixel value calculation unit.

For example, when a pixel with a pixel value exceeding a threshold value of 100 is set as an unintended display target in display setting unit 20, adjacent pixels of a search point $P_{ji}$ are eight pixels constituted by pixels belonging to an intended display area shown in black and pixel Q belonging to an unintended display area, as shown in FIG. 4, the pixel values of the pixels belong to the intended display area are 80, 85, 85, 90, 90, 95, and 95 respectively; and the pixel value of the pixel belonging to the unintended display area is 200, the pixel value of pixel Q belonging to the unintended display area may be replaced with a maximum value of 95 of pixel values of other adjacent pixels belonging to the intended display area. Here, the pixel value of pixel Q may be replaced with the average value of pixel values of other adjacent pixels belonging to the intended display area or with a fixed value like, for example, zero when MIP processing is performed or a maximum possible pixel value when MinIP processing is performed.

The pixel value g ($P_{ji}$) at each search point $P_{ji}$ is obtained by performing a linear interpolation on eight adjacent pixels forming a grid that includes the search point $P_{ji}$, as shown in FIG. 4. Here, when the coordinate points of the search point $P_{ji}$ is assumed to be (x, y, z), the pixel value g (x, y, z) may be obtained by Formula (1) below.

$$G(x,y,z)=a_0+a_1x+a_2y+a_3z+a_4xy+a_5yz+a_6zx+a_7xyz \quad (1)$$

More specifically, by substituting the coordinate ($x_k$, $y_l$, $z_m$) (k, l, and m=1, 2, - - - ) of each of eight pixels shown in FIG. 4 and the pixel value g ($x_k$, $y_l$, $z_m$) at each coordinate position to Formula (1) above, an equation with eight unknowns with respect to $a_t$ is obtained, and after $a_t$ (t=0 to 7) is determined, the coordinate value (x, y, z) of the search point $P_{ji}$ is substituted to obtain the pixel value g (x, y, z).

Note that for the pixel value of the adjacent pixel in the non-display area, a pixel value after the replacement described above is used in the interpolation operation.

Here, the description has been made of a case in which a pixel value g ($P_{ji}$) at each search point $P_{ji}$ is obtained by performing a linear interpolation on eight adjacent pixels forming a grid that includes the search point $P_{ji}$. Alternatively, the pixel value may be obtained by performing a tricubic interpolation on 64 pixels (four pixels in x-axis, y-axis, and z-axis directions respectively) forming a grid that includes the search point $P_{ji}$.

Next, based on the pixel value g ($P_{ji}$) at each search point $P_{ji}$, projection value determination unit 50 determines an output pixel value $C_j$ of each pixel on the projection plane.

For example, a maximum/minimum value of pixel values of all search points on each visual line $E_j$ may be determined as the output pixel value of the pixel projected by the visual line $E_j$ (MIP/MinIP processing) or an average value of pixel values of all search points on each visual line $E_j$ may be determined as the output pixel value of the pixel projected by the visual line E. Alternatively, a product of luminance value and opacity at each search point $P_{ji}$ is added up along each visual line $E_j$ and the added-up result is determined as the output pixel value $C_j$ of the projected pixel on the projection plane through which the visual line $E_j$ passes through (volume rendering method).

This processing is performed on each visual line to determine the output pixel values of all pixels projected on the projection plane, thereby generating a projection image (maximum value projection image/minimum value projection image). The generated projection image is displayed on the display of workstation 3 by image display unit 70.

As described above, in three-dimensional medical image processing system according to an embodiment of the present invention, when generating a projection image formed of each pixel on a projection plane by setting a plurality of search points in an intended display area of a three-dimensional image along a plurality of visual lines, each connecting each pixel on the projection plane on which the three-dimensional image is projected and an arbitrary viewpoint by search point setting unit 30, calculating a pixel value of each search point by pixel value calculation unit 40 by an interpolation operation based on pixel values of adjacent pixels of each search point, and determining a pixel value of each pixel on the projection plane with respect to each visual line by projection value determination unit 50 based on the calculated pixel value of each search point, if an adjacent pixel of a search point is a pixel in an unintended display area (unintended search point setting area), pixel value calculation unit 40 calculates the pixel value of the search point such that the pixel value of the pixel in the unintended search point setting area does not contribute to the calculation. Thus, a pixel value of a pixel in an unintended search point setting area does not influence in determining a pixel value of each pixel on a projection plane, whereby an artifact arising from an unintended search point setting area may be prevented.

It will be appreciated that various changes and modifications made in the system configuration, process flow, module configuration, and the like without departing from the spirit of the present invention are included in the technical scope of the present invention. The embodiment described above is provided by way of example and any part of the description should not be construed as limiting the technical scope of the invention.

For example, in the embodiment described above, both image processing and image display are carried out in image processing workstation 3, but the image processing may be performed by a separate image processing server additionally provided and connected to network 9. This allows distributed processing which, for example, may eliminate the need to provide a plurality of high performance image processing workstations where an image is displayed on a plurality of terminals, whereby the overall system cost is reduced.

The invention claimed is:

1. An image processing apparatus comprising a projection image generation means for setting a plurality of search points in a three-dimensional image along a plurality of visual lines, each connecting each pixel on a projection plane on which the three-dimensional image is projected and an arbitrary viewpoint, calculating a pixel value of each search point by an interpolation operation based on pixel values of adjacent pixels of each search point, determining a pixel value of each pixel on the projection plane with respect to each visual line based on the pixel values of the search points, and generating a projection image formed of each pixel on the projection plane, wherein:
the three-dimensional image is an image divided into an intended setting area in which the search points are intended to be set and the image is displayed and an unintended setting area in which the search points are not intended to be set and the image is not displayed;
the search points are in the intended setting area; and
the projection image generation means calculates the pixel value of the search point such that the pixel value of an adjacent pixel of the search point does not contribute to the calculation only on condition that the adjacent pixel is a pixel in the unintended setting area.

2. The image processing apparatus of claim 1, wherein the projection image generation means is a means that replaces the pixel value of the adjacent pixel in the unintended setting area with a value calculated from a pixel value of a pixel in the intended setting area using a method predetermined according to a determination method of the pixel values of the pixels on the projection plane and uses the post replacement value in the interpolation operation as the pixel value of the adjacent pixel in the unintended setting area.

3. The image processing apparatus of claim 1, wherein the projection image generation means is a means that replaces the pixel value of the adjacent pixel in the unintended setting area with a fixed value determined according to a determination method of the pixel values of the pixels on the projection plane and uses the post replacement value in the interpolation operation as the pixel value of the adjacent pixel in the unintended setting area.

4. The image processing apparatus of claim 1, wherein the projection image generation means is a means that replaces the pixel value of the adjacent pixel in the unintended setting area with a value not greater than a maximum value of pixel values of pixels in the intended setting area and determines a maximum value of pixel values of all search points on each visual line as the pixel value of each pixel on the projection plane corresponding to each visual line.

5. The image processing apparatus of claim 4, wherein the projection image generation means is a means that replaces the pixel value of the adjacent pixel in the unintended setting area with a value not greater than a maximum value of pixel values of adjacent pixels in the intended setting area adjacent to the search point with respect to the adjacent pixel in the unintended setting area.

6. The image processing apparatus of claim 5, wherein the three-dimensional image is an image divided such that a pixel value of a pixel in the unintended setting area is greater than a pixel value of a pixel in the intended setting area.

7. The image processing apparatus of claim 4, wherein the three-dimensional image is an image divided such that a pixel value of a pixel in the unintended setting area is greater than a pixel value of a pixel in the intended setting area.

8. The image processing apparatus of claim 1, wherein the projection image generation means is a means that replaces the pixel value of the adjacent pixel in the unintended setting area with a value not less than a minimum value of pixel values of pixels in the intended setting area and determines a minimum value of pixel values of all search points on each visual line as the pixel value of each pixel on the projection plane corresponding to each visual line.

9. The image processing apparatus of claim 8, wherein the projection image generation means is a means that replaces the pixel value of the adjacent pixel in the unintended setting area with a value not less than a minimum value of pixel values of adjacent pixels in the intended setting area adjacent to the search point with respect to the adjacent pixel in the unintended setting area.

10. The image processing apparatus of claim 9, wherein the three-dimensional image is an image divided such that a pixel value of a pixel in the unintended setting area is smaller than a pixel value of a pixel in the intended setting area.

11. The image processing apparatus of claim 8, wherein the three-dimensional image is an image divided such that a pixel value of a pixel in the unintended setting area is smaller than a pixel value of a pixel in the intended setting area.

12. An image processing method, comprising the steps of setting a plurality of search points in a three-dimensional image along a plurality of visual lines, each connecting each pixel on a projection plane on which the three-dimensional image is projected and an arbitrary viewpoint, calculating a pixel value of each search point by an interpolation operation based on pixel values of adjacent pixels of each search point, determining a pixel value of each pixel on the projection plane with respect to each visual line based on the pixel values of the search points, and generating a projection image formed of each pixel on the projection plane, wherein:
the three-dimensional image is an image divided into an intended setting area in which the search points are intended to be set and the image is displayed and an unintended setting area in which the search points are not intended to be set and the image is not displayed;
the search points are in the intended setting area; and
when calculating a pixel value of each search point, calculating the pixel value of the search point such that the pixel value of an adjacent pixel of the search point does not contribute to the calculation only on condition that the adjacent pixel is a pixel in the unintended setting area.

13. A non-transitory computer readable recording medium on which is recorded an image processing program for causing a computer to set a plurality of search points in a three-dimensional image along a plurality of visual lines, each connecting each pixel on a projection plane on which the three-dimensional image is projected and an arbitrary viewpoint, to calculate a pixel value of each search point by an interpolation operation based on pixel values of adjacent pixels of each search point, to determine pixel values of pixels on the projection plane with respect to each visual line based on the pixel values of the search points, and to generate a projection image formed of each pixel on the projection plane, wherein:
the three-dimensional image is an image divided into an intended setting area in which the search points are intended to be set and the image is displayed and an unintended setting area in which the search points are not intended to be set and the image is not displayed;
the search points are in the intended setting area; and
when calculating a pixel value of each search point, the pixel value of the search point is calculated such that the pixel value of an adjacent pixel of the search point does not contribute to the calculation only on condition that the adjacent pixel is a pixel in the unintended setting area.

* * * * *